US00PP29640P2

(12) United States Plant Patent
Smith

(10) Patent No.: US PP29,640 P2
(45) Date of Patent: Sep. 4, 2018

(54) ***VERBENA* PLANT NAMED 'RIKA18302M'**

(50) Latin Name: *Verbena hybrida*
Varietal Denomination: RIKA18302M

(71) Applicant: Tom Smith, Carleton, MI (US)

(72) Inventor: Tom Smith, Carleton, MI (US)

(73) Assignee: Plant 21, LLC, Bonsall, CA (US)

( * ) Notice: Subject to any disclaimer, the term of this patent is extended or adjusted under 35 U.S.C. 154(b) by 0 days.

(21) Appl. No.: 15/731,522

(22) Filed: Jun. 21, 2017

(51) Int. Cl.
*A01H 5/02* (2018.01)

(52) U.S. Cl.
USPC ..... Plt./308

(58) Field of Classification Search
USPC ..... Plt./308
See application file for complete search history.

(56) References Cited

PUBLICATIONS

PLUTO Plant Variety Database Mar. 17, 2018. p. 1.*

* cited by examiner

*Primary Examiner* — Annette H Para
(74) *Attorney, Agent, or Firm* — C. A. Whealy

(57) ABSTRACT

A new and distinct cultivar of *Verbena* plant named 'RIKA18302M', characterized by its compact, outwardly spreading and mounding to eventually trailing plant habit; vigorous growth habit; freely branching habit; dark green-colored leaves; freely flowering habit; light violet blue and white bi-colored flowers that are held at or above and beyond the foliar plane; and relative resistance to Powdery Mildew (*Podosphaera xanthii*).

1 Drawing Sheet

Botanical designation: *Verbena hybrida.*
Cultivar denomination: 'RIKA18302M'.

BACKGROUND OF THE INVENTION

The present invention relates to a new and distinct cultivar of *Verbena* plant, botanically known as *Verbena hybrida*, and hereinafter referred to by the name 'RIKA18302M'.

The new *Verbena* plant is a naturally-occurring branch mutation of *Verbena hybrida* 'RIKAV18302', disclosed in U.S. Plant Pat. No. 25,396. The new *Verbena* plant was discovered and selected by the Inventor on a single flowering plant within a population of plants of 'RIKAV18302' in a controlled greenhouse environment in Carleton, Mich. on Jun. 20, 2015.

Asexual reproduction of the new *Verbena* plant by vegetative terminal cuttings in a controlled environment in Carleton, Mich. since Jun. 22, 2015, has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'RIKA18302M'. These characteristics in combination distinguish 'RIKA18302M' as a new and distinct *Verbena* plant:

1. Compact, outwardly spreading and mounding to eventually trailing plant habit.
2. Vigorous growth habit.
3. Freely branching habit.
4. Dark green-colored leaves.
5. Freely flowering habit.
6. Light violet blue and white bi-colored flowers that are held at or above and beyond the foliar plane.
7. Relatively resistant to Powdery Mildew (*Podosphaera xanthii*).

Plants of the new *Verbena* can be compared to plants of the mutation parent, 'RIKAV18302'. Plants of the new *Verbena* differ primarily from plants of 'RIKAV18302' in flower color as plants of 'RIKAV18302' have dark violet-colored flowers.

Plants of the new *Verbena* can be compared to plants of the *Verbena hybrida* 'AKIV572-1', disclosed in U.S. Plant Pat. No. 23,050. In side-by-side comparisons, plants of the new *Verbena* differ primarily from plants of 'AKIV572-1' in the following characteristics:

1. Plants of the new *Verbena* are more vigorous than plants of 'AKIV572-1'.
2. Plants of the new *Verbena* have larger flowers than plants of 'AKIV572-1'.
3. Plants of the new *Verbena* and 'AKIV572-1' differ in flower color as plants of 'AKIV572-1' have solid light violet-colored flowers.
4. Plants of the new *Verbena* are more resistant to Powdery Mildew than plants of 'AKIV572-1'.

Plants of the new *Verbena* can also be compared to plants of the *Verbena hybrida* 'Vepita Lavender Ice', not patented. In side-by-side comparisons, plants of the new *Verbena* differ primarily from plants of 'Vepita Lavender Ice' in the following characteristics:

1. Plants of the new *Verbena* are more freely branching than plants of 'Vepita Lavender Ice'.
2. Plants of the new *Verbena* have larger flowers than plants of 'Vepita Lavender Ice'.
3. Plants of the new *Verbena* are more resistant to Powdery Mildew than plants of 'Vepita Lavender Ice'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'RIKA18302M' grown in a container.

The photograph at the top of the sheet is a close-up view of a typical flowering plant of 'RIKA18302M'.

DETAILED BOTANICAL DESCRIPTION

The aforementioned photographs and following observations and measurements describe plants grown during the early spring in 11.5-cm containers in an acrylic-covered greenhouse in Carleton, Mich. and under cultural practices typical of commercial *Verbena* production. During the production of the plants, day and night temperatures ranged from 18° C. to 27° C. Plants were eleven weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'RIKA18302M'.

Parentage: Naturally-occurring branch mutation of *Verbena hybrida* 'RIKAV18302', disclosed in U.S. Plant Pat. No. 25,396.

Propagation:

*Type cutting*.—Vegetative terminal cuttings.

*Time to initiate roots, summer*.—About three days at temperatures ranging from about 16° C. to 29° C.

*Time to initiate roots, winter*.—About four days at temperatures ranging from about 16° C. to 21° C.

*Time to produce a rooted plant, summer*.—About 15 days at temperatures ranging from about 16° C. to 29° C.

*Time to produce a rooted plant, winter*.—About 20 days at temperatures ranging from about 16° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, mounding and upright to eventually trailing plant habit; freely branching habit with about eight primary lateral branches developing per plant each with secondary branches potentially developing at every node; pinching is not required; dense and bushy plant habit; vigorous growth habit.

*Plant height, soil level to top of foliar plane*.—About 9.8 cm.

*Plant height, soil level to top of floral plane*.—About 11.5 cm.

*Plant diameter* (*spread*).—About 34 cm by 38 cm.

Lateral branch description:

*Length*.—Variable, about 21 cm.

*Diameter*.—About 2 mm.

*Internode length*.—About 3.3 cm.

*Orientation*.—Initially upright then outwardly spreading to trailing.

*Strength*.—Strong.

*Texture and luster*.—Pubescent; matte.

*Color, developing*.—Close to 146B.

*Color, developed*.—Close to 146A.

Leaf description:

*Arrangement*.—Opposite, simple.

*Length*.—About 4.2 cm.

*Width*.—About 2.8 cm.

*Shape*.—Roughly deltoid.

*Apex*.—Broadly acute.

*Base*.—Truncate.

*Margin*.—Crenate.

*Texture and luster, upper and lower surfaces*.—Pubescent, coarse; matte.

*Venation pattern*.—Pinnate; reticulate.

*Color*.—Developing leaves, upper and lower surfaces: Close to 146A. Fully expanded leaves, upper surface: Close to N137A; venation, close to 146B. Fully expanded leaves, lower surface: Close to 147B; venation, close to 146C.

*Petioles*.—Length: About 9 mm. Diameter: About 2.5 mm. Strength: Moderately strong. Texture and luster, upper and lower surfaces: Minute pubescence; matte. Color, upper and lower surfaces: Close to 146C.

Flower description:

*Flower arrangement and habit*.—Sessile salverform flowers arranged in upright hemispherical terminal racemes; flowers face upward or outwardly; freely flowering habit with about 20 flowers developing per inflorescence and typically more than 500 flowers developing per plant.

*Natural flowering season*.—Plants flower continuously from spring until frost in Michigan; early flowering habit, plants begin flowering about six weeks after planting.

*Flower longevity*.—Flowers last about four to five days on the plant; petals not persistent and sepals persistent.

*Fragrance*.—None detected.

*Inflorescence height*.—About 3.2 cm.

*Inflorescence diameter*.—About 5.8 cm.

*Flower buds*.—Length: About 1.8 cm. Diameter: About 3 mm. Shape: Elongated oblong. Texture and luster: Minute pubescence; matte. Color: Close to 91B.

*Flower diameter*.—About 2 cm by 2.2 cm.

*Flower depth* (*height*).—About 3.4 cm.

*Throat diameter*.—About 1.5 mm.

*Tube length*.—About 2.5 cm.

*Tube diameter, distally*.—About 2 mm.

*Corolla*.—Arrangement: Single whorl of five fused petals fused towards the base into a narrow tube and distally flaring abruptly. Petal lobe length: About 1.2 cm. Petal lobe width: About 1.1 cm. Petal lobe shape: Roughly cordate. Petal lobe apex: Emarginate. Petal margin: Entire; undulate. Petal texture and luster, upper surface: Smooth, glabrous; velvety, matte. Petal texture and luster, lower surface: Minute pubescence near tube; matte. Throat texture: Minute pubescence; matte. Tube texture: Minute pubescence; matte. Color: Petal, when opening and fully opened, upper surface: Alternating stripes, close to 92A and NN155D; venation, close to 92A and NN155D; color does not change with development. Petal, when opening and fully opened, lower surface: Alternating stripes, close to 92B and NN155D; venation, close to 92B and NN155D; color does not change with development. Throat: Close to 145D; venation, close to 145D. Tube: Close to 145C to 145D; venation, close to 145C to 145D.

*Calyx*.—Arrangement: Single whorl of five fused sepals fused towards the base into a slender tube. Calyx length: About 1.4 cm. Calyx diameter: About 2.5 mm. Sepal length: About 1.2 cm. Sepal width: Less than 1 mm. Sepal shape: Narrowly lanceolate. Sepal apex: Acute. Sepal margin: Entire. Sepal texture and luster, inner surface: Smooth, glabrous; slightly glossy. Sepal texture and luster, outer surface: Minute pubescence; matte. Sepal color: When opening and fully opened, upper surface: Close to 145B. When opening and fully opened, lower surface: Close to 146A.

*Peduncles*.—Length: About 3 cm. Diameter: About 2 mm. Strength: Strong. Aspect: Upright to about 45° from vertical. Texture and luster: Pubescent; matte. Color: Close to 146A.

*Reproductive organs*.—Stamens: Quantity and arrangement: Four per flower, filaments partially adnate to corolla tube. Filament length: About 1 cm. Filament color: Close to 145D. Anther shape: Round. Anther size: About 1 mm by 1 mm. Anther color: Close to 151A. Pollen amount: Scarce. Pollen color: Close to 151D. Pistils: Quantity: One per flower. Pistil length: About 2.2 cm. Stigma shape: Bi-parted. Stigma diameter: About 1 mm. Stigma color: Close to 144A. Style length: About 2 cm. Style color: Close to 145B. Ovary color: Close to 144A. Fruits and seeds: Fruit and seed development have not been observed on plants of the new *Verbena* to date.

Temperature tolerance: Plants of the new *Verbena* have been observed to tolerate temperatures from about 2° C. to about 40° C. and are suitable for USDA Hardiness Zones 8 to 11.

Pathogen & pest resistance: Plants of the new *Verbena* have been observed to be relatively resistant to Powdery Mildew (*Podosphaera xanthii*). Plants of the new *Verbena* have not been observed to be resistant to pests and other pathogens common to *Verbena* plants.

It is claimed:

1. A new and distinct *Verbena* plant named 'RIKA18302M' as illustrated and described.

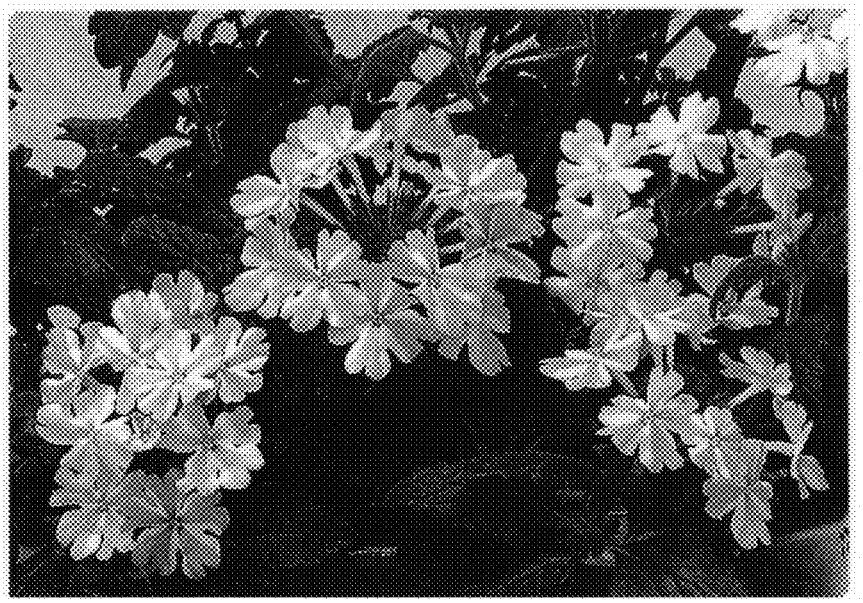
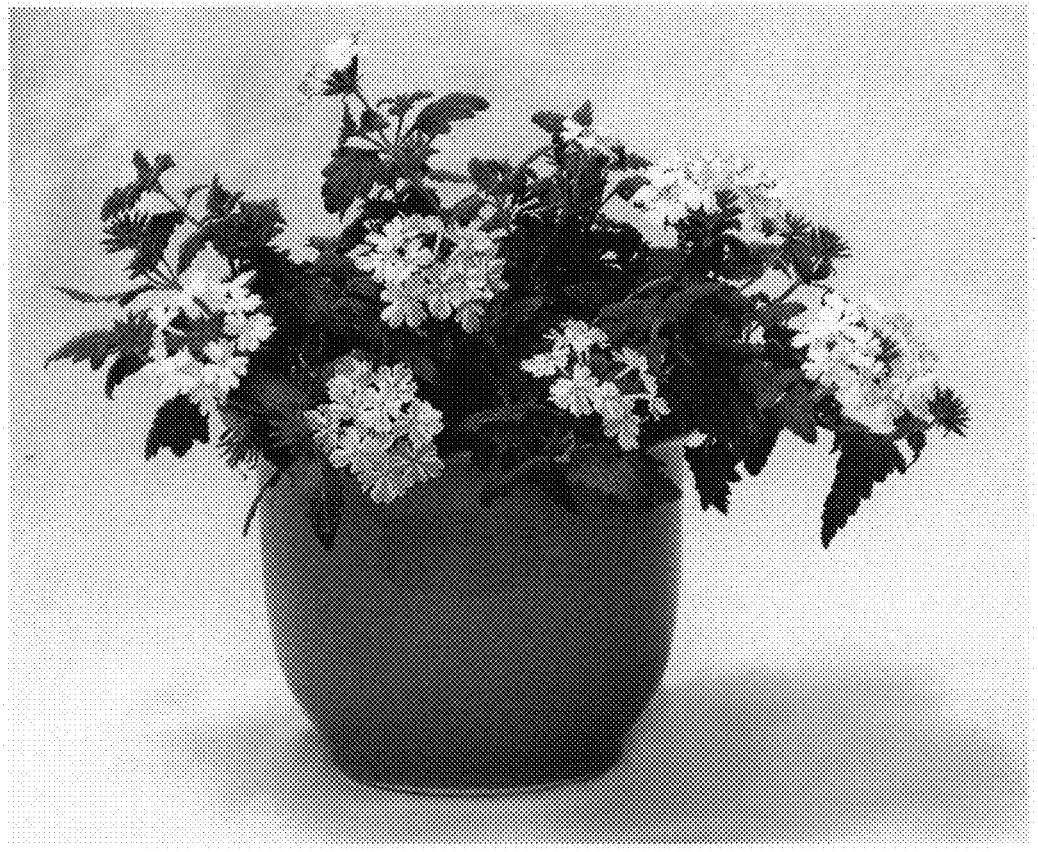

* * * * *